US008603525B2

(12) United States Patent
Oury et al.

(10) Patent No.: US 8,603,525 B2
(45) Date of Patent: *Dec. 10, 2013

(54) MULTILAYER ORALLY DISINTEGRATING TABLET

(75) Inventors: Pascal Oury, Le Chesnay (FR); Catherine Herry, Saint Pierre les Elbeuf (FR); Didier Hoarau, Montreal (CA)

(73) Assignee: Ethypharm (FR)

( * ) Notice: Subject to any disclaimer, the term of this patent is extended or adjusted under 35 U.S.C. 154(b) by 147 days.

This patent is subject to a terminal disclaimer.

(21) Appl. No.: 12/376,065

(22) PCT Filed: Jul. 31, 2007

(86) PCT No.: PCT/EP2007/057913
§ 371 (c)(1),
(2), (4) Date: Apr. 16, 2009

(87) PCT Pub. No.: WO2008/015221
PCT Pub. Date: Feb. 7, 2008

(65) Prior Publication Data
US 2009/0311320 A1 Dec. 17, 2009

Related U.S. Application Data

(60) Provisional application No. 60/821,455, filed on Aug. 4, 2006.

(51) Int. Cl.
A61K 9/24 (2006.01)
A61K 9/20 (2006.01)
A61K 9/26 (2006.01)
A61K 38/00 (2006.01)
A61K 31/60 (2006.01)

(52) U.S. Cl.
USPC ........... 424/472; 424/464; 424/465; 424/469; 514/18.4; 514/159; 514/165

(58) Field of Classification Search
None
See application file for complete search history.

(56) References Cited

U.S. PATENT DOCUMENTS

| 6,375,957 | B1 | 4/2002 | Kaiko et al. |
| 7,175,857 | B2 | 2/2007 | Petereit et al. |
| 2003/0092724 | A1 | 5/2003 | Kao et al. |
| 2003/0224051 | A1* | 12/2003 | Fink et al. .................... 424/473 |
| 2006/0204578 | A1* | 9/2006 | Vergez et al. ................. 424/473 |
| 2007/0036861 | A1 | 2/2007 | Oury et al. |
| 2009/0304792 | A1* | 12/2009 | Hoarau .......................... 424/465 |

FOREIGN PATENT DOCUMENTS

| EP | 0548356 | B1 | 1/1997 |
| EP | 0636364 | B1 | 9/2000 |
| EP | 1003484 | B1 | 11/2001 |
| EP | 1058538 | B1 | 6/2002 |
| WO | 9301805 | A1 | 2/1993 |
| WO | 9846215 | A1 | 10/1998 |
| WO | 9904763 | A1 | 2/1999 |
| WO | 0006126 | A1 | 2/2000 |
| WO | 0027357 | A1 | 5/2000 |
| WO | 0051568 | A1 | 9/2000 |
| WO | 2004110411 | A3 | 12/2004 |
| WO | WO 2004/110411 | * | 12/2004 |

OTHER PUBLICATIONS

Machine Translation for Oury et al. WO 2004/110411 provided in pdf form.*
Seager, "Drug-delivery Products and the Zydis Fast-dissolving Dosage Form", J. Pharm. Pharmacol, vol. 50, pp. 375-382 (1998).
Remington'S Pharmaceutical Sciences, 17th Ed., Chapter 76 p. 1418 (1985).
International Search Report for PCT/EP2007/057913 dated Jun. 11, 2008.

* cited by examiner

Primary Examiner — Robert A Wax
Assistant Examiner — Jeffrey T Palenik
(74) Attorney, Agent, or Firm — Caesar, Rivise, Bernstein, Cohen & Pokotilow, Ltd.

(57) ABSTRACT

An orally disintegrating multilayer tablet comprising at least two discrete layers, one of which comprises at least one active agent that promotes the oxidation of opioids, preferably acetaminophen, and the other of which contains granules including an inert core which is coated with at least one opioid and at least one binder, wherein said opioid coating is coated with a subcoat comprising a compound soluble in gastric fluids, said subcoat being coated with a taste-masking coating comprising a polymer or copolymer comprising dialkylaminoalkyl(meth)acrylate units and a pore-forming agent.

20 Claims, No Drawings

MULTILAYER ORALLY DISINTEGRATING TABLET

The present invention relates to a multilayer orally disintegrating tablet and to the process for preparing it.

Various orally disintegrating tablets are currently available on the market. These tablets include a disintegrating agent and usually a pharmaceutically active ingredient ("active ingredient") and disintegrate or dissolve without a chewing action in less than three minutes, usually in less than 60 seconds, upon contact with saliva, forming a suspension of small particles which is easy to swallow.

Once easily swallowed, the particles containing the active ingredient release the same most preferably into the stomach or into the upper part of the gastrointestinal tract.

This type of tablet is described, for example, in EP 548 356, EP 636 364, EP 1 003 484, EP 1 058 538, WO 98/46215, WO 00/06126, WO 00/27357 and WO 00/51568.

The small particles, also called granules, contain the active ingredient, which may have a bitter or unpleasant taste. In this case, the active ingredient or the granules may be film-coated, thus preventing a bad taste from developing in the mouth. Such coating can also be provided to prevent the active ingredient from being prematurely released in the mouth or to ensure delayed release in the stomach.

Orally disintegrating tablets are a convenient route for swallowing active agents since they do not require, but not exclude, absorbing water at the same time.

Owing to its ease of use, the orally disintegrating tablet is entirely suitable for ambulatory treatment, more particularly for certain patients and especially the elderly or young children, who have difficulties in swallowing such that they find it unpleasant, or even impossible, to ingest tablets or gel capsules, even with a simultaneous intake of liquid.

In this regard, it is estimated that 50% of the population experiences such difficulties, with the possible consequence of the prescribed medicinal product not being taken and thus a major impact on the efficacy of the treatment (H. Seager, 1998, J. Pharm. Pharmacol. 50, 375-382).

These difficulties in swallowing are obviously exacerbated when several medicinal products need to be taken throughout the day, thus multiplying the number of administrations.

Orodispersible tablets comprising fixed combinations of active substances would thus represent a solution of choice for improving the patient compliance with long-term treatments, in the case of chronic pathologies.

For instance, it would be highly desirable to provide for orally disintegrating tablets including both an opioid such as oxycodone and acetaminophen, in order to manage moderate to severe pain.

Conventional tablets including a combination of oxycodone with acetaminophen are currently being marketed by ENDO PHARMACEUTICALS under the trademark Percocet®.

However, formulating orally disintegrating tablets including both oxycodone and acetaminophen proved to be difficult, since it has been discovered that acetaminophen can promote the degradation of an opiate such as oxycodone by direct interaction especially in moist conditions or in the presence of residual humidity.

It has also been observed that acetaminophen release was slowed down when acetaminophen crystals were coated with oxycodone hydrochloride in taste masked granules dispersed within an orally disintegrating tablet.

For the purposes of the present invention the expression "orally disintegrating tablets" refers to a tablet which disintegrates or dissolves in the mouth in less than 60 seconds, preferably in less than 40 seconds upon contact with saliva, without chewing, forming therefore a suspension which is easy to swallow.

The disintegration time here corresponds to the time between the moment when the tablet is placed on the tongue and the moment when the suspension resulting from the disintegration or dissolution of the tablet is swallowed.

Thus, there remains a need for orally disintegrating tablets in which a peroxide-sensitive active agent such as oxycodone can be stably included together with acetaminophen without experiencing any substantial degradation.

The present inventors have discovered that this need could be satisfied by formulating acetaminophen or another active agent that promotes oxidation of opioids and an opioid such as oxycodone in separate layers of the same multilayer orally disintegrating tablet.

Such a multilayer tablet has already been disclosed in WO 2004/110411. It is comprised of an orodispersible tablet allowing the combination of various active substances, without having the drawbacks of non-uniformity of content. This tablet design also enables to formulate together two active ingredients such as oxycodone hydrochloride (which is an opioid) and paracetamol (acetaminophen) that are incompatible with each other.

Since oxycodone hydrochloride is known to have a bitter taste, following the teaching of WO 2004/110411, it will be desirable to apply directly thereto a taste-masking coating, usually based on an acrylate copolymer sold by RÖHM PHARMA POLYMERS (Degussa) as EUDRAGIT® E100.

However, the Applicant has also unexpectedly observed that the oxycodone content tends to decrease with time in the orodispersible tablets containing oxycodone hydrochloride directly coated with EUDRAGIT®E100 and demonstrated that this was due to oxycodone hydrochloride degradation, which is hypothesized to be due to some interactions between the hydrogen atoms of the ammonium function of oxycodone hydrochloride and the nitrogen atom of the tertiary amines of the dimethylaminoethyl methacrylate units of EUDRAGIT® E100, without intending to be bound by any theory.

Therefore, there remains the need for a means for orally delivering to the gastrointestinal tract a stable and non-bitter form of an opioid such as oxycodone, in the presence of acetaminophen, while avoiding premature release thereof in the mouth.

Extensive research has thus been conducted so as to limit the degradation of oxycodone in multilayer fast disintegrating tablets, which led to the present invention.

Thus, the present invention relates to an orally disintegrating multilayer tablet comprising at least two discrete layers, one of which comprises at least one active agent that promotes oxidation of opioids, such as acetaminophen, and the other of which contains granules containing an inert core which is coated with at least an opioid and at least a binder, wherein said opioid coating is coated with a subcoat comprising a compound soluble in gastric fluids, said subcoat being coated with a taste-masking coating comprising a polymer or copolymer comprising dialkylaminoalkyl(meth)acrylate units and optionally a pore-forming agent.

The number of layers in the multilayer orally disintegrating tablet is limited by the resulting thickness of the tablet, which must be acceptable to the patient, and generally does not exceed three.

In a first variant of the invention, the orally disintegrating tablet is a bi-layer tablet comprising at least one active substance in each layer.

In a second variant of the invention, the orally disintegrating tablet is a three-layer tablet. In this case, the three layers may each contain an active substance or one of the layers may contain only excipients.

Advantageously, the layer containing only excipients is inserted between the two layers respectively comprising the active agent (such as acetaminophen) and an opioid.

The opioid may be chosen from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures thereof or any of their pharmaceutically acceptable salts.

The expression "pharmaceutically acceptable" is used herein to refer to compounds, materials, compositions and/or pharmaceutical forms that are, according to what is commonly medically accepted, suitable for use on contact with human or animal tissues without toxicity, irritation, allergic response or other excessive problem or complication, for a reasonable benefit/risk ratio.

The expression "pharmaceutically acceptable salts" means the derivatives of the described compounds in which the base pharmaceutically active compound is converted into its basic or acidic salt. Examples of pharmaceutically active salts especially comprise the organic acid or mineral acid salts of basic residues such as amines; the alkaline derivatives or the organic salts of acidic residues such as carboxylic acids, and the like. The pharmaceutically acceptable salts comprise the standard non-toxic salts or the quaternary ammonium salts of the base compound, formed, for example, from non-toxic mineral or organic acids. For example, such standard non-toxic salts comprise those derived from mineral acids such as hydrochloric acid, hydrobromic acid, hydroiodic acid, sulphuric acid, sulphonic acid, sulphamic acid, phosphoric acid, nitric acid, boric acid and the like; and the salts prepared from organic acids such as amino acids, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, gluconic acid, malonic acid, mandelic acid, glutamic acid, glutaric acid, benzoic acid, salicylic acid, sulphanilic acid, 2-acetoxybenzoic acid, fumaric acid, benzenesulphonic acid, p-toluenesulphonic acid, methanesulphonic acid, ethanedisulphonic acid, camphorsulphonic acid, oxalic acid, isethionic acid, glycerophosphoric, pantothenic acid, salicylic acid, succinic acid, tartaric acid, terephthalic acid and the like.

The pharmaceutically acceptable salts of the present invention may be synthesized from the base therapeutic compound which contains an acidic or basic fraction, via standard processes. In general, these salts may be prepared by reacting the free acid or free base forms with a predetermined amount of the appropriate base or acid in water or in an organic solvent or in a mixture of water and organic solvent.

Non-aqueous media are generally preferred. The lists of suitable salts are given in Remington's Pharmaceutical Sciences, 17th ed., Mack Publishing Company, Easton, Pa., 1985, p. 1418.

A preferred opioid is oxycodone, which may be used as such or preferably as one of its salts, more preferably as oxycodone hydrochloride. The multilayer tablet of this invention may preferably comprise from 1 to 20 mg and more preferably from 2.5 to 10 mg oxycodone hydrochloride.

"Opioid" will be used indifferently in the following description to designate either the base compounds or their pharmaceutically acceptable salts.

The active agent that promotes oxidation of opioids is one that, under storage conditions of 25° C. and 60% relative humidity or 40° C. and 75% relative humidity, promotes the oxidation of at least one opioid such as oxycodone when blended therewith or when the opioid is coated on the active agent. This active agent is preferably acetaminophen. The multilayer tablet of this invention may preferably comprise from 100 to 750 mg and more preferably from 250 to 500 mg acetaminophen.

The active agent (such as acetaminophen) may be in the form of powder or microcrystals, or in the form of granules obtained by dry, wet or hot granulation, or alternatively in the form of granules obtained by coating onto neutral cores, for instance in a fluid bed coater device, or by extrusion-spheronization. The active agent is used in dry form for granulation, and in the form of a solution or suspension in an aqueous or organic solvent for coating onto neutral cores.

The neutral cores onto which the opioid and optionally the active agent (such as acetaminophen) are separately applied may consist independently of any chemically and pharmaceutically inert excipient, existing in particulate, crystalline or amorphous form, for example sugar derivatives such as lactose, sucrose, hydrolysed starch (maltodextrins) or celluloses. Mixtures such as sucrose and starch, or cellulose-based mixtures may also be used for the preparation of neutral cores. A sugar core is preferred in the present invention. The unit particle size of the neutral core may be between 50 μm and 500 μm and preferably between 90 μm and 250 μm.

The opioid coating may be applied by spraying a suspension or solution of opioid onto the neutral cores, preferably in a fluid bed coater device. Preferably, the opioid will be used as a suspension in a hydroalcoholic medium. It has indeed been observed that using a hydroalcoholic medium instead of an aqueous medium provided for greater stability of the opioid. The hydroalcoholic medium advantageously comprises water and ethanol, for instance in a ratio of ethanol to water ranging from about 60:40 to about 92:8 and more preferably of about 75:25. The present inventors have discovered that this solvent reduced the opioid degradation.

The opioid layer also comprises a binding agent or binder. Said binder is conventionally used in proportions that can range up to 95% by weight relative to the dry weight of the coating, preferably up to 50% by weight relative to the dry weight of the opioid coating.

Its function is to bind the active ingredient to the neutral core without loss of material, or to "bond" the powder or the microcrystals of opioid and the other excipients, in order to give a homogeneous layer of pharmaceutically active ingredient, evenly distributed around the neutral core.

The binder can be chosen from the group consisting of cellulose-based polymers, such as hydroxypropylmethylcellulose, hydroxypropylcellulose and hydroxyethylcellulose; acrylic polymers; polyvinyl alcohols; alginic acid or sodium alginate; starch or pregelatinized starch; sucrose and derivatives thereof; guar gum; polyethylene glycols, and mixtures and copolymers thereof, for instance a graft copolymer of polyvinyl alcohol and polyethylene glycol, such as sold by BASF under trade name KOLLICOAT® IR.

Hydroxypropylmethylcellulose (also referred to as "HPMC" hereunder) is the preferred binder according to this invention. It can preferably be chosen from those for which the apparent viscosity (aqueous solution at 2% wt/wt, at 20° C., USP method) is between 2.4 and 18 mPa·s, and even more preferably between 2.4 and 5 mPa·s.

The binder, when dissolved in a hydroalcoholic solvent, is advantageously present in a proportion that can range up to 90%, preferably of between 5% and 60% and more preferably of about 50% by weight relative to the weight of opioid.

Moreover, the opioid layer may also comprise one or more pharmaceutically acceptable excipients, apart from the binding agent.

The pharmaceutically acceptable excipients optionally present may be chosen from surfactants, antistatic agents, lubricants, and mixtures thereof.

The surfactant, which is optionally present in the opioid coating, can be chosen from cationic, anionic, nonionic or amphoteric agents, alone or as a mixture.

The surfactant can be chosen, for example, from compounds such as sodium lauryl sulphate, the monooleate, the monolaurate, the monopalmitate, the monostearate, the trioleate, the tristearate or any other ester of polyoxyethylenated sorbitan, preferably Tween® 20, 40, 60 or 80, glycerides of polyoxyethylenated fatty acids, these fatty acids being saturated or unsaturated and composed of at least 8 carbon atoms, poloxamers, such as poloxamer 188, ethylene oxide/propylene oxide block copolymers, such as Pluronic® F68 or F87, lecithin, stearyl alcohol, cetyl alcohol, cholesterol, polyoxyethylenated castor oil, fatty alcohol polyoxyethylenated ethers, such as the Brij® products, and polyoxyethylenated stearates.

The surfactant is advantageously present in a proportion that can range up to 20%, preferably of between 0.1 and 20% by weight relative to the total dry weight of the coating.

The antistatic agent can be used in a proportion that can range up to 10% by weight, relative to the dry weight of the coating applied around the neutral core. The antistatic agent may be chosen from the group consisting of: colloidal silica and preferably precipitated silica, micronized or non-micronized talc, and mixtures thereof.

The lubricant may be selected from the group comprising magnesium, zinc, and calcium stearate, stearic acid, talc, pyrogenic silica, sodium stearylfumarate, micronized polyoxyethylene glycol (micronized Macrogol 6000), leucine, sodium benzoate, and mixtures thereof.

The layer comprising the opioid is further coated by a separating layer (also referred to as "subcoat") between the coating layer comprising the opioid and the taste-masking polymeric layer, wherein said subcoat comprises at least a compound soluble in gastric fluids, i.e. in highly acidic conditions (pH comprised between 1 and 3), preferably a polymer which can be chosen among the binding polymers or copolymers mentioned above. An example of a copolymer that can be used in the subcoat is a graft copolymer of polyvinyl alcohol and polyethylene glycol, such as sold by BASF under the trade name KOLLICOAT® IR. A preferred polymer is hydroxypropylmethylcellulose. The polymer or copolymer, included within the subcoat, acts as a separating layer in order to avoid direct contact between the opioid layer and the taste-masking polymer, and dissolves rapidly without altering opioid release. The subcoat layer may also comprise an antistatic agent such as those listed previously.

The subcoat is advantageously present in a proportion that can range up to 50%, preferably of between 5% and 30% by weight relative to the weight of opioid coated cores.

The subcoat can be applied by conventional means, such as in a fluid bed coater device, by spraying a solution or a dispersion of binder in an aqueous or preferably in a hydroalcoholic medium onto the cores coated with the opioid. The hydroalcoholic medium advantageously comprises water and ethanol, for instance in a ratio of ethanol to water ranging from about 60:40 to about 92:8 and more preferably of about 85:15.

Of course, opioid coating and the subcoat do not include any polymer comprising dialkylaminoalkyl(meth)acrylate units.

This subcoat is itself coated by a taste-masking coating layer comprising a polymer or copolymer comprising dialkylaminoalkyl(meth)acrylate units, such as dimethylaminoethyl methacrylate units. This polymer can be, for instance, a copolymer of dimethylaminoethyl methacrylate, methylmethacrylate and n-butyl methacrylate, such as the copolymer sold by RÖHM PHARMA POLYMERS (Degussa) under the trade names EUDRAGIT® E100 and EPO.

The taste-masking coating preferably further includes a pore-forming agent which can be a hydrophilic polymer soluble in gastric fluids, such as hydroxypropylmethylcellulose or other polymers used as binders such as polyvinylpyrrolidone, polyvinylalcohol, polyethyleneglycols, or a soluble agent, preferably chosen from the group of sugars such as sucrose, lactose or dextrose, of polyols such as mannitol, sorbitol or lactitol, or of organic acids and their salts such as citric acid, tartaric acid, succinic acid, or else of inorganic salts such as sodium chloride. A preferred pore-forming agent is hydroxypropylmethylcellulose.

The pore-forming agent, which is present in the taste-masking coating, can be used in a proportion that can range up to 50%, preferably of between 5% and 30% by weight relative to the total dry weight of the taste-masking coating ingredients.

It has indeed been shown that the provision of this pore-forming agent within the taste-masking coating improved the release rate of the opioid from the granule at a pH equal or greater than pH 5.5 such as in the intestine, by increasing the permeability of the taste-masking film coating and thus preventing the slowing down of opioid release when the granules directly pass into the intestine, which may undesirably occur when the patient ingesting the granule has a fast digestion and/or is stressed.

The amount of pore-forming agent in the taste-masking coating and the total amount of taste-masking coating relative to the total weight of the opioid granule with its subcoat have to be chosen so as to ensure fast dissolving in pH equal or greater than pH 5.5 and to provide taste-masking effectiveness. The ratio of the taste-masking coating to the total dry weight of ingredients comprising the opioid granule with its subcoat ranges from about 10:90 to about 50:50 and more preferably is of about 20:80 (or 25%).

The taste-masking layer may also comprise an antistatic agent, such as those listed above.

According to this invention, the above-described opioid granules are included with the active agent (such as acetaminophen) in separate layers of an orally disintegrating multi-layer tablet.

The active agent can be provided as crystals or as granules wherein it can be coated with a taste-masking coating. The excipients included within this taste-masking coating can be the same as listed above. In this case, the taste-masking coating of the opioid granules and the taste-masking coating of the active agent granules can be the same or different.

In a preferred embodiment, the crystals of active agent (such as acetaminophen) are granulated with a binder and the obtained granules are coated with a taste-masking coating.

In a most preferred embodiment, the crystals of active agent are directly coated with a taste-masking coating.

Each of the layers of the tablet according to this invention usually comprises a mixture of tableting excipients. This mixture comprises:
  at least one soluble agent and
  at least one disintegrating agent and/or at least one swelling agent.

The soluble agent may be chosen from sugars such as sucrose, lactose, fructose, dextrose or polyols containing less than 13 carbon atoms, such as mannitol, xylitol, sorbitol, maltitol, lactitol or erythritol, alone or as a mixture. Preferably, sorbitol is not used alone but in a mixture with at least one other soluble agent.

The soluble agent is generally used in a proportion of between 20% and 90% by weight and preferably between 30% and 60% by weight, relative to the weight of each layer of the tablet.

In the case where only one soluble agent is used, it is under directly compressible form, the mean particle diameter of which is from 100 µm to 500 µm. In the case where a mixture of at least two soluble agents is used, at least one is under the directly compressible product form, the other one being under the form of a powder whose mean particle diameter is less than 100 µm.

Each layer of the tablet may comprise a single soluble agent or a mixture of at least two soluble agents.

The tablet may comprise the same soluble agent in each of the layers or the same mixture of soluble agents, but the composition may also vary from one layer to another, not only as regards the nature of the soluble agent and the size of the particles thereof, but also, in the case of a mixture, the ratio of each of the fractions.

In a first advantageous embodiment of the tablet of the invention, each layer of the tablet contains a single soluble agent used in its directly compressible form.

In a second advantageous embodiment of the tablet of the invention, each layer of the tablet contains a mixture comprising a soluble agent in its directly compressible form and the same soluble agent in its powder form, the respective proportions of the directly compressible form and of the powder being between 99/1 and 20/80 and preferably between 80/20 and 20/80, said soluble agent not being sorbitol.

In this regard, the soluble agent is preferably a mixture of mannitol in the form of a powder with an average particle size of less than 100 µm, preferably Mannitol 60 and directly compressible mannitol with an average particle size from 100 to 500 µm, such as Mannitol 300.

In a third advantageous embodiment of the tablet of the invention, the tablet contains the same soluble agent or the same mixture of soluble agents in each of the layers of which it is composed.

The disintegrating agent may be selected from the group especially comprising crosslinked sodium carboxymethylcellulose denoted in the art by the term croscarmellose, crosslinked polyvinylpyrrolidones, denoted in the art by the term crospovidones, and mixtures thereof.

The disintegrating agent may be used in a proportion of between 1% and 20% by weight and preferably between 5% and 15% by weight, in the case of a mixture, each disintegrant being between 0.5% and 15% by weight and preferably between 5% and 10% by weight, relative to the weight of each layer of the tablet.

Crospovidone is preferred for a use in this invention. Indeed, it has been observed that crospovidone had a stabilizing effect on the degradation of an opioid such as oxycodone hydrochloride, when the orodispersible tablets are stored under a dry and hot atmosphere such as 60 or 80° C. dry heat in Aluminium/Aluminium blister pockets. In these conditions, the crospovidone catches and sequestrates the residual water of the granules. However these storage conditions are not conventional. The tablets according to the invention are rather generally packaged in sealed containers such as blisters which are stored in ambient or conventional temperature/humidity conditions as per ICH guidelines. Actually, under moist conditions such as 40° C./75% HR, crospovidone swells with water and favors water uptake in the tablet which promotes the diffusion of residual peroxides in the matrix. In order to avoid this drawback, the tablets can advantageously include an anti-oxidant agent so as to better protect the opioid from degradation which could occur under moist conditions as a result of crospovidone degradation.

Preferably, said anti-oxidant is present only in the opioid layer.

Examples of suitable anti-oxidants include ascorbic acid and its salts and esters, such as sodium ascorbate and ascorbyl palmitate; and tocopherol and its esters such as tocopherol acetate.

Usually, the anti-oxidant is present from 0.2 to 1 wt % relative to the total weight of the layer comprising the opioid. It can also be expressed as a ratio to the crospovidone used. In this regard, it is preferred that the anti-oxidant represents from 1 to 5% of the weight of the crospovidone used in the layer comprising the opioid.

In particular, it has been found that ascorbyl palmitate efficiently prevented degradation of crospovidone under moist conditions and thus protected the opioid from oxidation. The amount of ascorbyl palmitate that can be included in the tablets according to this invention can range from 0.2 to 1 wt % relative to the total weight of the layer comprising the opioid. It can also be expressed as a ratio to the crospovidone used. In this regard, it is preferred that ascorbyl palmitate represents from 1 to 5% of the weight of the crospovidone used in the layer comprising the opioid.

The swelling agent can be selected from the group consisting of microcrystalline cellulose, starches, modified starches, such as carboxymethylstarch or sodium glycolate starch, alginic acid or sodium alginate, and mixtures thereof.

The swelling agent is generally used in a proportion of between 1% and 15% by weight, relative to the weight of each layer of the tablet.

Besides the excipients mentioned above, each layer of the orally disintegrating tablet of the invention may optionally comprise a lubricant, a permeabilizing agent, an antistatic agent, a water-insoluble diluent, a binder, a sweetener, a flavouring, a colorant and adjuvants.

The lubricant may be selected from the group comprising magnesium stearate, stearic acid, sodium stearyl fumarate, polyoxyethylene glycols, sodium benzoate, a pharmaceutically acceptable oil, preferably dimethicone or liquid paraffin, and mixtures thereof.

The lubricant is generally used in a proportion that may be up to 2%, preferably between 0.02% and 2% by weight and more preferably between 0.5% and 1.5% by weight, relative to the weight of each layer of the tablet.

In a first variant, all the lubricant is incorporated into the mixture of tableting excipients. In a second variant, a fraction of this lubricant is sprayed onto the walls of the die and the punches at the time of compression, said lubricant fraction then being in the form of a powder or a liquid.

The amounts of lubricant optionally used in the internal and/or external phase are carefully adjusted so as to prevent an excess from adversely affecting the cohesion of the layers at the time of the final compression.

The permeabilizing agent may be selected from the group especially comprising silicas with great affinity for aqueous solvents, such as the precipitated silica more commonly known under the brand name Syloid®maltodextrins and β-cyclodextrins, and mixtures thereof.

The permeabilizing agent is generally used in a proportion that may be up to 5% by weight, calculated relative to the weight of each layer of the tablet.

The antistatic agent may be selected from the group consisting of micronized or non-micronized talc, colloidal silica (Aerosil®200), treated silica (Aerosil®R972) or precipitated silica (Syloid® FP244) and mixtures thereof.

The antistatic agent is generally used in a proportion that may be up to 5% by weight, relative to the weight of each layer of the tablet.

The water-insoluble diluent may be selected from dicalcium phosphate, tricalcium phosphate and a microcrystalline cellulose.

Its function is to improve the action of the disintegrating agent by increasing the insoluble charge in the tablet. It is used in a proportion that may be up to 20% by weight and preferably less than 10% by weight, relative to the weight of each layer of the tablet.

The binder is generally used in dry form and may be a starch, a sugar, polyvinylpyrrolidone or carboxymethyl-cellulose, alone or as a mixture.

The sweetener may be selected from the group especially comprising aspartame, potassium acesulfame, sodium saccharinate, neohesperidine dihydrochalcone, sucralose and monoammonium glycyrrhizinate, and mixtures thereof.

The flavourings and colorants are those usually used in pharmacy for the preparation of tablets.

In one particularly preferred embodiment, each layer has a different colour from that of the layer to which it is attached, such that the layered structure of the tablet is immediately visible.

Adjuvants may also be added to the mixture, and may be chosen from the group comprising disintegration accelerators, for example amino acids or proteins, pH adjusters, systems for producing effervescence, especially carbon dioxide generators of the type used as pH adjusters, or surfactants.

In a layer comprising a pharmaceutically active substance, the proportion of the mixture of excipients relative to the coated or uncoated active substance is usually between 0.4 and 10 and preferably between 1 and 5 parts by weight.

In one advantageous embodiment of the tablet of the invention, each layer of the tablet comprises the same excipients, so that the disintegration of the tablet of the invention affords a mouthfeel that is identical to that afforded by a "monolayer" orally disintegrating tablet of the same qualitative composition, and so that the patient does not perceive any difference in the rate of disintegration between the various layers of which the tablet is composed.

The quantitative composition of each layer is adjusted to take account of the contents of each active substance.

The maximum mass ratio tolerated between the thickest layer and the thinnest layer is 10/1.

In the case where the dose ratio between the most heavily dosed active substance and the most lightly dosed active substance is greater than 10, the amount of diluent is adjusted such that the weight ratio between the layers is brought back to a value of 10. In this case, the diluent is preferably a soluble agent, more preferably a soluble agent in a directly compressible form.

The tablets may have a diameter of between 6 mm and 18 mm.

They may have a round, oval or oblong shape, they may have a flat, concave or convex surface, and they may optionally be engraved. Punches of biconvex shape or dimple shape are advantageously used.

The tablets generally have a weight of between 0.1 gram and 2.0 grams.

The invention also relates to the process for preparing the multilayer tablets described above.

The process in accordance with the invention comprises the following steps:

1. preparing optionally coated particles of an active agent that promotes the degradation of opioids, such as acetaminophen;
2. preparing granules comprising an opioid coating applied onto a neutral core, the opioid coating comprising an opioid and at least one binder and being coated with a subcoat comprising a compound soluble in gastric fluids, said subcoat being itself coated with a taste-masking coating comprising a polymer or a copolymer comprising dialkylaminoalkyl(meth)acrylate units and optionally a pore-forming agent;
3. preparing at least two dry mixtures each comprising tableting excipients, one of which contains said active agent particles and the other of which contains the above granules;
4. precompressing at least one of the powder mixtures obtained above;
5. applying another mixture to the above mixture
6. optionally precompressing
7. finally compressing the preformed layers obtained above, steps 5 and 6 possibly being repeated at least once depending on the number of layers of the tablet.

In the case of a bi-layer tablet, the process in accordance with the invention comprises the following steps 4 to 7:
   precompressing one of the above mixtures so as to preform the lower layer of the tablet,
   applying the second mixture to the preformed layer,
   optionally, precompressing the second mixture so as to pre-form the upper layer of the tablet,
   finally compressing.

In any case, Step 2 preferably comprises applying the opioid coating by spraying a suspension of the opioid in a hydroalcoholic medium onto neural cores, since this embodiment provides for greater stability of the opioid.

Moreover, in one preferred embodiment, the preparation of each mixture itself comprises two steps, the first step consisting in mixing the coated or uncoated active substance with all of the tableting excipients except for the lubricant, followed by a second step in which the lubricant is totally or partially added to the first mix, the optionally remaining portion then being sprayed onto the punches and/or onto the inner face of the dies.

When all of the lubricant is sprayed onto the punches and/or onto the inner face of the dies, the second mixing step is then obviously omitted.

The precompression and compression steps are performed on an alternating or rotary tableting machine.

The precompression is intended on the one hand to preform the layer by packing the bed of powder in the die, and secondly to remove gas from the said bed of powder, by reorganizing the particles, so as to avoid the appearance of cleavage at the time of the final compression, this cleavage possibly arising either between the layers, due to lack of adhesion, or within the layer itself.

In a tablet whose layers do not have the same relative mass and/or thickness magnitude, the first preformed layer is the one of larger mass or thickness.

The stresses exerted during the precompression step may range from 0.5 to 15 kN and are generally 5 to 10 times lower than the stresses exerted during the final compression.

The stresses exerted during the compression step may range from 5 kN to 50 kN and preferably from 5 kN to 15 kN.

The precompression forces applied to the beds of powder are adjusted according to two possible modes, the first consisting in adjusting the compression force as a function of the variations measured by the machine regarding the heights of the bed of powder in the die, and the second consists in adjusting the filling volume as a function of the measured pressure exerted by the punches.

The hardness of these tablets is preferably between 10 and 100 N and more preferably between 10 and 60 N, measured according to the method of the European Pharmacopoeia (2.9.8).

The hardness of the multilayer tablet is adapted so as to obtain a friability, measured according to the method of the European Pharmacopoeia, of less than 2% and preferably less than 1%, and so as to allow a disintegration time of the tablet in the mouth under the action of saliva of less than or equal to 60 seconds and preferably less than or equal to 40 seconds.

Since the tablet of the invention contains an opioid and possibly also another active agent (such as acetaminophen) in coated form, the compression should usually be performed so as to maintain an identical dissolution profile between the coated active substance particles before and after compression, the term "identical" necessarily meaning not differing by more than 15% as an absolute value relative to the percentage of active substance released at each sampling time under the same in vitro dissolution conditions.

The multilayer disintegrating tablets according to this invention can be used to relieve moderate to severe pain and preferably in the management of breakthrough pain, in particular breakthrough cancer pain, by oral administration, generally to patients which are tolerant to opioid therapy. Breakthrough pain means a transitory flare of pain of moderate to severe intensity occurring on a background of otherwise controlled pain. Patients considered opioid tolerant are those who are taking at least 60 mg morphine/day, at least 25 μg transdermal fentanyl/hour, at least 30 mg of oxycodone daily, at least 8 mg of oral hydromorphone daily or an equianalgesic dose of another opioid for a week or longer.

This invention thus also pertains to the use of the aforementioned tablets for the manufacture of an analgesic medicament for oral administration, intended in particular to reduce breakthrough pain. It also pertains to a method for reducing pain comprising oral administration of a tablet as described above.

The invention will be understood more clearly by means of the following examples which are given purely for the purpose of illustrating advantageous embodiments of the invention, and do not in any way constitute a limitation thereof.

EXAMPLES

Example 1

Preparation of Granules Entrapping Oxycodone

Neutral cores were introduced into a fluid bed processor and a suspension of oxycodone hydrochloride and hydroxypropylmethyl cellulose (HPMC) as a binder in a solvent of water and ethanol was sprayed on the neutral cores. The composition of oxycodone pellets is given in Table 1. The oxycodone amount entrapped in the pellets was of 9.78% (97.8 mg/g). A subcoat was then applied to the oxycodone pellets. The subcoat contained HPMC and silicon dioxide (as an antistatic) in a water/ethanol solvent as shown in Table 2. After drying, the granules were again introduced to the fluid bed processor and coated with a taste-masking coating of Eudragit® E100 acrylic polymer, HPMC and silicon dioxide in a water/ethanol solvent as shown in Table 3. In a last step, before discharging the taste-masked oxycodone granules, an antistatic solution composed of a suspension of silicon dioxide in ethanol was sprayed into the fluid bed processor. The composition is given in table 4. The oxycodone amount entrapped in the final granules was of 6.5% (65.0 mg/g).

TABLE 1

Composition of oxycodone hydrochloride pellets

| MATERIALS | % | TOTAL WEIGHT (KG) |
|---|---|---|
| Neutral cores | 85.33 | 14.18 |
| LAYERING SOLUTION | | |
| Oxycodone | 9.78 | 1.626 |
| HPMC | 4.89 | 0.813 |
| Water | n/a* | 4.96* |
| Ethanol | n/a* | 18.00* |
| Total (dry) | 100.00 | 16.62 |

*solvent removed during process

TABLE 2

Composition of oxycodone granules with the applied subcoat

| MATERIALS | % | TOTAL WEIGHT (KG) |
|---|---|---|
| Oxycodone pellets | 83.5 | 16.62 |
| SUBCOATING SOLUTION | | |
| HPMC | 15 | 2.99 |
| Syloid F244P | 1.5 | 0.3 |
| Water | n/a* | 4.04* |
| Ethanol | n/a* | 22.92* |
| Total (dry) | 100 | 19.90 |

*solvent removed during process

TABLE 3

Composition of the taske-masking coating

| MATERIALS | % | TOTAL WEIGHT (KG) |
|---|---|---|
| Oxycodone granules | 79.74 | 19.90 |
| COATING SOLUTION | | |
| Eudragit E100 | 14.74 | 3.68 |
| HPMC | 3.68 | 0.92 |
| Syloid F244P | 1.84 | 0.46 |
| Water | n/a* | 14.17* |
| Ethanol | n/a* | 21.26* |
| Total | 100 | 24.96 |

*solvent removed during process

TABLE 4

Excipients used in the antistatic suspension applied
on the taste-masked oxycodone granules

| MATERIALS | % | TOTAL WEIGHT (KG) |
|---|---|---|
| Taste-masked oxycodone granules | 99.8 | 24.96 |
| ANTISTATIC SOLUTION | | |
| Syloid F244P | 0.2 | 0.05 |
| Ethanol | n/a* | 0.83* |
| Total | 100 | 25.01 |

*solvent removed during process

Example 2

Preparation of Orally Disintegrating Multilayered Tablets

This example describes the preparation of bilayer tablets of oxycodone and acetaminophen.

Taste-masked granules of oxycodone are prepared according to example 1 (oxycodone content: 65.0 mg/g).

Coated crystals of acetaminophen, with 6% of taste-masking coating, are prepared in a fluid-bed coater according to the formula given in Table 5 (APAP content: 940.00 mg/g).

TABLE 5

Composition of the coated crystals of acetaminophen

| Material | % | Total weight (kg) |
|---|---|---|
| Acetaminophen crystals | 94.00 | 23.5 |
| Eudragit E100 | 2.99 | 0.747 |
| Eudragit NE30D | 1.49 | 0.374 |
| Syloid 244 FP | 1.52 | 0.379 |
| Ethanol 96 | n/a* | 23.11* |
| Total (dry) | 100 | 25.0 |

*removed during drying step

Bilayer tablets are then made, which have the composition given in Table 6.

TABLE 6

Composition of the bilayer tablets
(oxycodone 5 mg/acetaminophen 325 mg)

| Material | Mass per unit (mg/tab) | Percent (%) |
|---|---|---|
| Layer 1 | | |
| Oxycodone coated granules | 76.92 | 8.78 |
| Mannitol 300 | 27.93 | 3.19 |
| Mannitol 60 | 27.93 | 3.19 |
| Crospovidone | 17.60 | 2.01 |
| Avicel PH102* | 17.60 | 2.01 |
| Aspartame | 3.52 | 0.40 |
| Ascorbyl palmitate | 0.53 | 0.06 |
| Silicone dioxide 244 FP | 0.88 | 0.10 |
| Strawberry flavour | 0.88 | 0.10 |
| Pink color | 0.12 | 0.01 |
| Magnesium stearate | 2.11 | 0.24 |
| Layer 2 | | |
| Acetaminophen coated crystals | 345.74 | 39.47 |
| Mannitol 300 | 92.43 | 10.55 |
| Mannitol 60 | 92.43 | 10.55 |
| Crospovidone | 70.00 | 7.99 |
| Avicel PH102* | 70.00 | 7.99 |
| Aspartame | 14.00 | 1.60 |
| Silicone dioxide 244 FP | 3.50 | 0.40 |
| Strawberry flavor | 3.50 | 0.40 |
| Magnesium stearate | 8.40 | 0.96 |
| Total | 876.0 | 100.00 |

*microcrystalline cellulose (FMC Corp)

The oxycodone blend is prepared as follows. Crospovidone, Avicel PH102, Aspartame, silicone dioxide, ascorbyl palmitate, flavor and colorant are blended in a cubic blender for 20 min at 10 rpm. Oxycodone coated granules, Mannitol 60 and Mannitol 300 are added to this blending and blended in a same cubic blender for 5 min at 10 rpm. Magnesium stearate is added and the final blend is 2 min at 10 rpm.

The colorant can be substituted by mannitol in order not to distinguish the opioid layer from the other layer.

The acetaminophen blend is prepared as follows. Crospovidone, Avicel PH102, Aspartame, silicone dioxide and flavor are blended in a cubic blender for 20 min at 10 rpm. Acetaminophen crystals, Mannitol 60 and Mannitol 300 are added to this blending and blended in a same cubic blender for 5 min at 10 rpm. Magnesium stearate is added and the final blend is 2 min at 10 rpm.

Compression Step:

Tabletting machine: FETTE 3090 double layer

Tablet size and shape: 15 mm, flat

The acetaminophen blend is the first to be filled in the compression matrix. Precompression is applied (pre-compression force: 0.5 kN) and compression volume is chosen to have an acetaminophen blend layer of about 700.0 mg. The oxycodone colored blend is then poured in the compression matrix to have an oxycodone blend mass of 176.0 mg for a 5 mg strength. Compression force is applied to obtain tablets with an hardness of 50 to 60 N. Using the same oxycodone blend and simply by varying the weight of the layer comprising oxycodone (Table 7), it is possible to obtain taste-masked bi-layer orally disintegrating tablets according to the present invention.

TABLE 7

Composition of bi-layer orally disintegrating
tablets comprising 325 mg of acetaminophen and
2.5 to 10 mg of oxycodone hydrochloride

| Oxycodone Dosage (mg) | 2.5 | 5 | 7.5 | 10 |
|---|---|---|---|---|
| Oxycodone Layer (mg) | 88.0 | 176.0 | 264.0 | 352.1 |
| Acetaminophen Layer (mg) | 700.0 | 700.0 | 700.0 | 700.0 |
| Tablet weight | 788.0 | 876.0 | 964.0 | 1052 |

The invention claimed is:

1. Orally disintegrating multilayer tablet comprising at least two discrete layers, one layer of which comprises at least one active agent that promotes the oxidation of opioids and the other layer of which contains opioid granules, said opioid granules including an inert core which is coated with at least one opioid and at least one binder, wherein said opioid coating is coated with a subcoat comprising a compound soluble in gastric fluids, wherein the subcoat limits the degradation of the opioid, said subcoat being coated with a taste-masking coating comprising a dialkylaminoalkyl(meth)acrylate copolymer and a pore-forming agent selected from the group consisting of a hydrophilic polymer soluble in gastric fluids and a binder, said opioid coating and said subcoat being free of any dialkylaminoalkyl(meth)acrylate copolymer.

2. Orally disintegrating multilayer tablet according to claim 1, wherein the tablet comprises 2 or 3 layers.

3. Orally disintegrating multilayer tablet according to claim 2, wherein the tablet comprises three layers, wherein a layer containing only excipients is inserted between the two layers respectively comprising acetaminophen and the opioid.

4. Orally disintegrating multilayer tablet according to claim 1, wherein the opioid is oxycodone or a pharmaceutically acceptable salt thereof.

5. Orally disintegrating multilayer tablet according to claim 4, wherein the opioid is oxycodone hydrochloride.

6. Orally disintegrating multilayer tablet according to claim 5, wherein the tablet comprises from 1 mg to 20 mg oxycodone hydrochloride.

7. Orally disintegrating multilayer tablet according to claim 1, wherein the tablet comprises from 100 mg to 750 mg acetaminophen as the at least one active agent that promotes oxidation of opioids.

8. Orally disintegrating multilayer tablet according to claim 1, wherein the inert core is a sugar core.

9. Orally disintegrating multilayer tablet according to claim 1, wherein said binder is chosen from the group consisting of: cellulose-based polymers; acrylic polymers; polyvinyl alcohols; alginic acid or sodium alginate; starch or pregelatinized starch; sucroses and derivatives thereof; guar gum; polyethylene glycols; and mixtures and copolymers thereof.

10. Orally disintegrating multilayer tablet according to claim 9, wherein the binder is hydroxypropylmethylcellulose, hydroxypropylcellulose or hydroxyethylcellulose.

11. Orally disintegrating tablet according to claim 1, wherein the compound soluble in gastric fluids is hydroxypropylmethylcellulose.

12. Orally disintegrating multilayer tablet according to claim 1, wherein the dialkylaminoalkyl(meth)acrylate copolymer is a copolymer of dimethylaminoethyl methacrylate, methylmethacrylate and n-butyl methacrylate.

13. Orally disintegrating multilayer tablet according to claim 1, wherein each layer comprises a mixture of excipients comprising:
   at least one soluble agent, and
   at least one disintegrating agent and/or at least one swelling agent.

14. Orally disintegrating multilayer tablet according to claim 13, wherein the disintegrating agent is crospovidone.

15. Orally disintegrating multilayer tablet according to claim 13, wherein said excipients in the opioid layer further comprise an anti-oxidant agent.

16. Orally disintegrating multilayer tablet according to claim 15, wherein said anti-oxidant agent is ascorbyl palmitate.

17. Method for preparing the tablet according to claim 1, comprising the following steps:
   1. preparing optionally coated particles of an active agent that promotes the oxidation of opioids;
   2. preparing granules comprising an opioid coating applied onto an inert core, the opioid coating comprising an opioid and at least one binder and being coated with a subcoat comprising a compound soluble in gastric fluids, said subcoat being coated with a taste-masking coating comprising a polymer, a copolymer comprising dialkylaminoalkyl (meth)acrylate units and a pore-forming agent;
   3. preparing at least two dry mixtures each comprising tableting excipients, one of which contains said active agent particles and the other of which contains the above granules;
   4. precompressing at least one of the dry mixtures obtained above;
   5. applying another mixture to the above mixture;
   6. optionally precompressing; and
   finally compressing the preformed layers obtained above, steps 5 and 6 possibly being repeated at least once depending on the number of layers of the tablet.

18. Method according to claim 17, wherein Step 2 comprises applying the opioid coating by spraying a suspension of the opioid in a hydroalcoholic medium onto the inert core.

19. Orally disintegrating multilayer tablet according to claim 1, wherein the at least one active agent that promotes the oxidation of opioids comprises acetaminophen.

20. Orally disintegrating multilayer tablet according to claim 1, wherein the pore-forming agent is hydroxypropylmethylcellulose.

* * * * *